(12) United States Patent
Maschke

(10) Patent No.: US 9,208,559 B1
(45) Date of Patent: Dec. 8, 2015

(54) METHOD AND APPARATUS FOR GASTRIC ARTERY CHEMICAL EMBOLIZATION

(71) Applicant: Siemens Aktiengesellschaft, Munich (DE)

(72) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/340,787

(22) Filed: Jul. 25, 2014

(51) Int. Cl.
  *G06K 9/00* (2006.01)
  *G06T 7/00* (2006.01)
  *G06T 11/60* (2006.01)
  *G06T 15/00* (2011.01)

(52) U.S. Cl.
  CPC ............ *G06T 7/0012* (2013.01); *G06T 7/0042* (2013.01); *G06T 11/60* (2013.01); *G06T 15/00* (2013.01); *G06T 2207/10116* (2013.01); *G06T 2207/30092* (2013.01); *G06T 2207/30101* (2013.01)

(58) Field of Classification Search
  USPC .................................................. 382/128–134
  See application file for complete search history.

(56) References Cited

U.S. PATENT DOCUMENTS

| | | | |
|---|---|---|---|
| 6,370,417 B1* | 4/2002 | Horbaschek et al. | 600/424 |
| 7,734,009 B2 | 6/2010 | Brunner et al. | |
| 7,822,241 B2* | 10/2010 | Eck et al. | 382/128 |
| 7,822,464 B2 | 10/2010 | Maschke et al. | |
| 7,918,793 B2* | 4/2011 | Altmann et al. | 600/437 |
| 7,996,060 B2* | 8/2011 | Trofimov et al. | 600/424 |
| 8,565,859 B2* | 10/2013 | Wang et al. | 600/427 |
| 2002/0065455 A1* | 5/2002 | Ben-Haim et al. | 600/407 |
| 2003/0014034 A1* | 1/2003 | Strobel | 604/407 |
| 2004/0138548 A1* | 7/2004 | Strommer et al. | 600/407 |
| 2004/0165766 A1* | 8/2004 | Goto | 382/154 |
| 2005/0196028 A1* | 9/2005 | Kleen et al. | 382/128 |
| 2005/0203369 A1* | 9/2005 | Sathyanarayana | 600/407 |
| 2006/0064006 A1* | 3/2006 | Strommer et al. | 600/415 |
| 2006/0241445 A1* | 10/2006 | Altmann et al. | 600/443 |
| 2007/0201609 A1* | 8/2007 | Ohishi et al. | 378/4 |
| 2008/0004530 A1* | 1/2008 | Feldman et al. | 600/467 |
| 2009/0088632 A1* | 4/2009 | Khamene et al. | 600/424 |
| 2009/0234444 A1 | 9/2009 | Maschke | |
| 2009/0310847 A1* | 12/2009 | Matsuzaki et al. | 382/132 |
| 2010/0074504 A1* | 3/2010 | Bruijns et al. | 382/132 |
| 2010/0114308 A1 | 5/2010 | Maschke | |
| 2011/0002513 A1* | 1/2011 | Molinari et al. | 382/128 |
| 2012/0300903 A1* | 11/2012 | Yao et al. | 378/62 |
| 2014/0099012 A1* | 4/2014 | Begin et al. | 382/131 |
| 2015/0131886 A1* | 5/2015 | Aben et al. | 382/132 |

* cited by examiner

OTHER PUBLICATIONS

Arepally et al. "Catheter-directed Gastric Artery Chemical Embolization Suprresses Systemic Ghrelin Levels in Porcine Model," Radiology, vol. 249, No. 1, (2008) pp. 127-133.

*Primary Examiner* — Alex Liew
(74) *Attorney, Agent, or Firm* — Schiff Hardin LLP

(57) ABSTRACT

In a method and an apparatus for implementing a gastric artery chemical embolization (GACE) catheterization procedure, an x-ray imaging system obtains a first current image data set of the patient prior to implementing the GACE procedure, and a second current image data set that shows the blood vessels that supply the fundus of the subject. The first and second current image data sets are fused to form a first fusion image data set. A second fusion image data set is then formed by fusion of the first fusion image data set with a catheter-position-indicating data set, obtained during the GACE procedure. The second fusion image data set is displayed during the GACE procedure or control data for a lightweight robot, used to operate and guide the catheter, can be derived from the second fusion image data set.

15 Claims, 4 Drawing Sheets

METHOD AND APPARATUS FOR GASTRIC ARTERY CHEMICAL EMBOLIZATION

BACKGROUND OF THE INVENTION

1. Field of the Invention

The present invention concerns a method for gastric artery chemical embolization making use of an imaging apparatus, as well as an imaging apparatus for implementing such a method.

2. Description of the Prior Art

Obesity is a serious physical illness that has important meaning, not only for the person affected, but also for society as a whole.

In an examination of the body mass index (BMI) distribution conducted in Germany, a rapid increase in BMI in recent years has been observed. Using BMI as an indicator for obesity, approximately a quarter of the population is obese.

The causes of being overweight are numerous. These include a familial disposition to obesity, genetic causes, modern lifestyle, such as lack of exercise and improper nutrition such as high consumption of protein-dense foods, fast food, sugar-containing drinks, and alcoholic beverages. Other sources of obesity are chronic stress, eating disorders, endocrine disorders such as hypothyroidism and Cushing syndrome, pharmaceuticals such as antidepressants, neuroleptics, anti-diabetics, beta blockers, etc. Other causes are enforced immobility, pregnancy, surgery in the hypothalamus region, and nicotine withdrawal.

Obesity is not always the result of a lack of self-discipline or abstinence on the part of the individual, as may sometimes be assumed by laymen, or even physicians. Obesity can be caused by a complex interaction of environmental factors, behavior-related factors, and genetic/biological bases.

Conventional treatments for obesity usually involve, as a first resort, a long-term adjustment of the nutrition and lifestyle habits of the patient. In order for such a treatment to be effective, the patient must be actively involved and must accept the fact that he or she has a weight problem, and must commit to the physician's instructed treatment. In such situations, however, caution is suggested in the case of pregnancy, lactation, or severe general illnesses. In such cases, this type of conventional treatment of obesity should be postponed until the general health of the patient improves.

Cornerstones of conventional obesity therapy are diet counseling, which includes calorie reductions, behavioral therapy, which may include relearning responses to feelings of hunger and satiation, and they also involve stress reduction and addressing eating disorders. A further cornerstone of conventional treatment is regular physical training and exercise.

Although subject to considerable variations, if and when body mass index is considered to be a reliable indicator of obesity, it is generally considered that a person with a BMI of 30 or more should be counseled to lose weight.

Overweight individuals can achieve significant health advantages by a reduction in weight. Lowering cholesterol level and the risk of related illnesses are beneficial. Among such illnesses are, for example, coronary heart disease, high blood pressure and arterial sclerosis. The risk of developing type 2 diabetes also drops significantly with weight reduction.

For persons for whom the aforementioned conventional treatment does not achieve meaningful results, a further option, implemented only by consultation with a knowledgeable physician, is a pharmaceutical treatment.

Pharmaceuticals such as the appetite suppressants Sibutramine and Rimonabant have previously been used for treating obesity. These appetite suppressants modify the brain metabolism and intensify the feeling of satiation. Such appetite suppressants, however, often lead to significant side effects, particularly if the patient has pre-existing cardiovascular disease. For these reasons, Rimonabant is no longer permitted for treatment of obesity. The approval for Sibutramine for obesity treatment has currently lapsed, and pharmaceuticals containing Sibutramine can no longer be dispensed through pharmacies. The manufacturer of that pharmaceutical has removed it from the market. Over the counter tablets with the active substance Orlistat are available for addressing obesity. Orlistat has previously been available only by prescription. This pharmaceutical inhibits the fat-digesting enzymes in the intestine, and thus reduces fat absorption. As a result, only a portion of the ingested fat is actually digested. The undigested portion of the fat exits the body. Among side effects of this pharmaceutical are diarrhea and increased flatulence. Moreover, such diet pills are effective only if the calorie intake is simultaneously limited and regular exercise is scheduled. Such diet pills are not a replacement for exercise or proper diet.

A very last resort to treating obesity, again to be considered only after consultation with a physician, is surgery. Surgery is generally considered as a viable alternative to extremely obese subjects, such as those having a BMI of 40 or more, or patients having a BMI of 35 or more who have significant related illnesses, such as type 2 diabetes. Surgery should only be considered as an option after exhausting all avenues of more conservative treatments.

Commonly available surgical procedures include reducing the size of the stomach (gastroplasty), and reducing the size of the entrance to the stomach with an adjustable stomach band. In this type of surgery, an adjustable silicone band is placed around the fundus of the stomach in a laparoscopic procedure. The diameter of the opening can be adjusted by selectively filling the band with a fluid. For this purpose, access to the band (i.e., a port) must be provided in the stomach wall or in the front of the sternum. A constriction of the stomach diameter thereby takes place in the intake region, and a long-term, significant weight reduction can be achieved.

Another surgical option is the implantation of a stomach balloon, which occupies a volume within the stomach that would otherwise be occupied by ingested food, thereby producing an artificial feeling of satiation.

Other surgical options involve intestinal procedures that produce a modified nutrient absorption.

Another surgical option has been recently developed that is a minimally invasive procedure that has shown success in animal experiments. This is known as the GACE procedure, and is described in "Catheter-Directed Gastric Artery Chemical Embolization Suppresses Systemic Ghrelin Levers in Porcine Model," Arepally, Radiology, Volume 249, No. 1 (2008).

In this procedure, a catheter is introduced via the femoral artery into the gastric artery. The gastric artery is an artery of the abdominal cavity in the region of the epigastrium, and essentially supplies the fundus of the stomach with blood.

The fundus is the dome-shaped, curved portion of the stomach that is situated next to, and to the left of, the stomach entrance (cardia). Air that is unavoidably swallowed with ingestion normally collects at this location. The fundus glands are found in the gastric mucosa of this portion of the stomach.

In the GACE procedure, a chemo-embolization of the gastric artery takes place via the catheter, thereby reducing the production of the hormone ghrelin, which is significantly produced in the cells of the walls of the fundus, and stimulates the feeling of hunger.

Initial results with the GACE procedure have shown that the feeling of hunger is reduced by the chemo-embolization, thereby leading to a decrease in weight.

A disadvantage of the GACE procedure is that the vascular supply of the fundus includes many overlapping vessels for blood supply to other organs, such as the liver. If the gastric artery is not properly targeted for the chemo-embolization, this can lead to an insufficient, incomplete or even an incorrect embolization. Conventional x-ray techniques such as fluoroscopy and 2D angiography have not been found to be satisfactory for reliably implementing the GACE procedure. This current situation has impaired the success rate of GACE procedures that have been implemented, and may possibly result in damage to other organs.

SUMMARY OF THE INVENTION

An object of the present invention is to provide an imaging apparatus and method that provides accurate guidance for a chemo-embolization catheter for implementing a GACE procedure in the gastric artery, making use of 2D and 3D x-ray imaging.

In accordance with the invention, before implementing the GACE catheterization procedure, a first, current image data set of the fundus is obtained with an x-ray imaging system, which is preferably a 3D image data set. A second current image data set is then obtained, which shows the blood vessels that supply the fundus, with the gastric artery being highlighted. This second, current data set also may be a 3D data set. The first and second current image data sets are used, so as to form a first fusion image data set.

A second fusion image data set is then formed by fusion of the first fusion image data set with a 2D image obtained during the GACE procedure in which the catheter is visible, or by fusion of the first image data set with position data that identify (designate) the position of the catheter during the GACE procedure. The resulting second fusion image data set shows not only the fundus and the blood vessels that supply the fundus, but also the current position of the catheter. This second fusion image is displayed during the GACE procedure to aid the physician in guiding the catheter in the GACE procedure.

Because the first current image data set and the second current image data set were acquired with the same x-ray imaging device, those images are already in registration, without further measures being necessary.

An apparatus for implementing the above method includes an x-ray imaging apparatus, such as a robotically-controlled C-arm x-ray system, and may also include a so-called lightweight robot (LWR) for operating and guiding the catheter. At various points in the inventive procedure, contrast agent may be injected, and thus the apparatus can also include a manually operated or automatically operated contrast agent injector. The apparatus also includes suitable display screens for presenting the relevant images during the course of the procedure.

DESCRIPTION OF THE PREFERRED EMBODIMENTS

Figure 1:
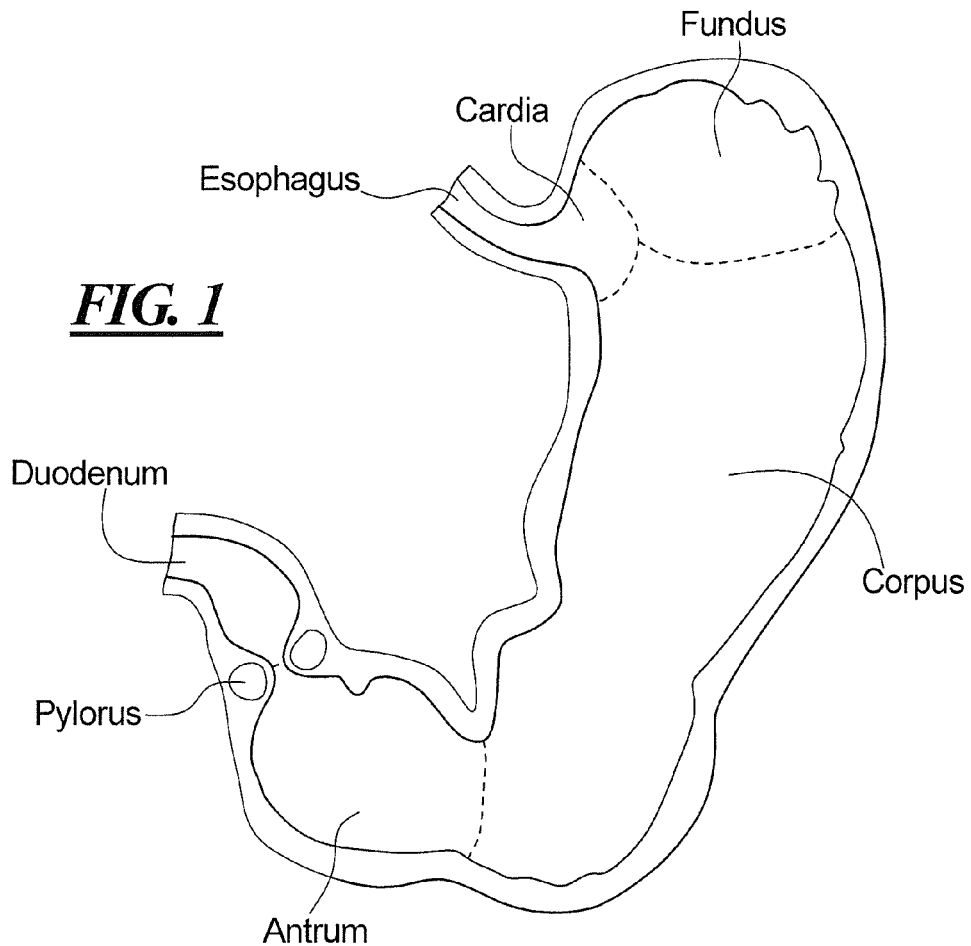
FIG. 1 schematically illustrates the basic regions of the human stomach.

For a better understanding of the details of the GACE procedure, the basic anatomy of the human stomach is schematically illustrated in FIG. 1. The internally-indicated regions of the human stomach do not have precise boundaries therebetween, but the generally-accepted, approximate boundaries between those regions are indicated by dashed lines in FIG. 1:

Ingested food and fluids enter the stomach via the esophagus, into a region designated as the cardia. The stomach has a dome-shaped region called the fundus that is generally above the esophagus, and the fundus transitions into the largest region of the stomach, called the corpus. The corpus, in turn, transitions into the lower part of the stomach known as the antrum. Digested food and fluid exit the stomach into the duodenum via the pyloric sphincter, or pylorus.

As noted above, the vasculature that feeds the stomach is complicated to visualize in an angiographic image. The most important arteries are schematically illustrated in FIG. 2, which is an anterior-to-posterior view, meaning that anatomy closer to the posterior is shown behind anatomy closer to the anterior.

Figure 2:
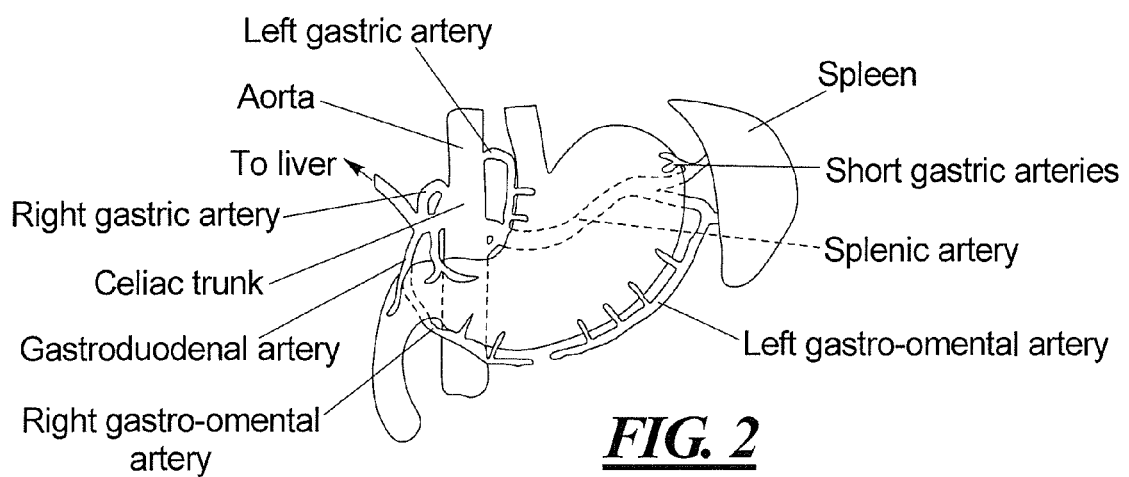
FIG. 2 schematically illustrates the major arteries that surround the human stomach.

The main artery feeding anatomy in the abdomen is the aorta, and the portion of the stomach noted above designated as the antrum is shown anterior to the aorta in FIG. 2. The stomach is fed with blood by the portion of the aorta known as the celiac trunk. From the celiac trunk, the splenic artery proceeds anterior to the corpus and the fundus, to the spleen.

The stomach is fed with blood from the left gastro-omental artery and the short gastric arteries, which branch from the splenic artery, as well as by the right gastro-omental artery and the gastroduodenal artery, which branch from the celiac trunk. The stomach is also fed with blood from the right gastric artery. The celiac trunk also feeds blood to the liver, as indicated in FIG. 2 by a further branch.

As can be seen in FIG. 2, the left gastro-omental artery is anterior to the stomach, the splenic artery is posterior to the stomach, a portion of the right gastro-omental artery is posterior to the stomach and a portion thereof also is anterior to the stomach, and the left gastric artery is anterior to the stomach.

Figure 3:
FIG. 3 is a DSA (Digital Subtraction Angiography) image of the celiac and superior mesenteric arteries, from the aforementioned article by Arepally et al., which illustrates the known catheter-directed GACE technique.

In the catheter-directed GACE procedure as described above, the catheter is conventionally guided by a DSA image of the relevant portion of the stomach, which is shown in FIG. 3, from the aforementioned article by Arepally et al. In this procedure, celiac artery angiography is performed in an anteriorposterior projection, in order to identify the celiac artery, two left gastric arteries (black arrow), and the left gastric artery (white arrow). Superselective catheterization of the arteries that supply the fundus is performed. For the GACE procedure, sodium morrhuate (50 mg/mL, 5%) was infused into the arteries that supply the fundus.

As can be seen from the DSA image in FIG. 3, the vascular supply of the fundus includes many overlapping vessels for blood supply to other organs, and it is important for the gastric artery to be properly targeted for the chemo-embolization. The conventional DSA image shown in FIG. 3 has proven not to be satisfactory for reliably implementing the GACE procedure.

Figure 4:
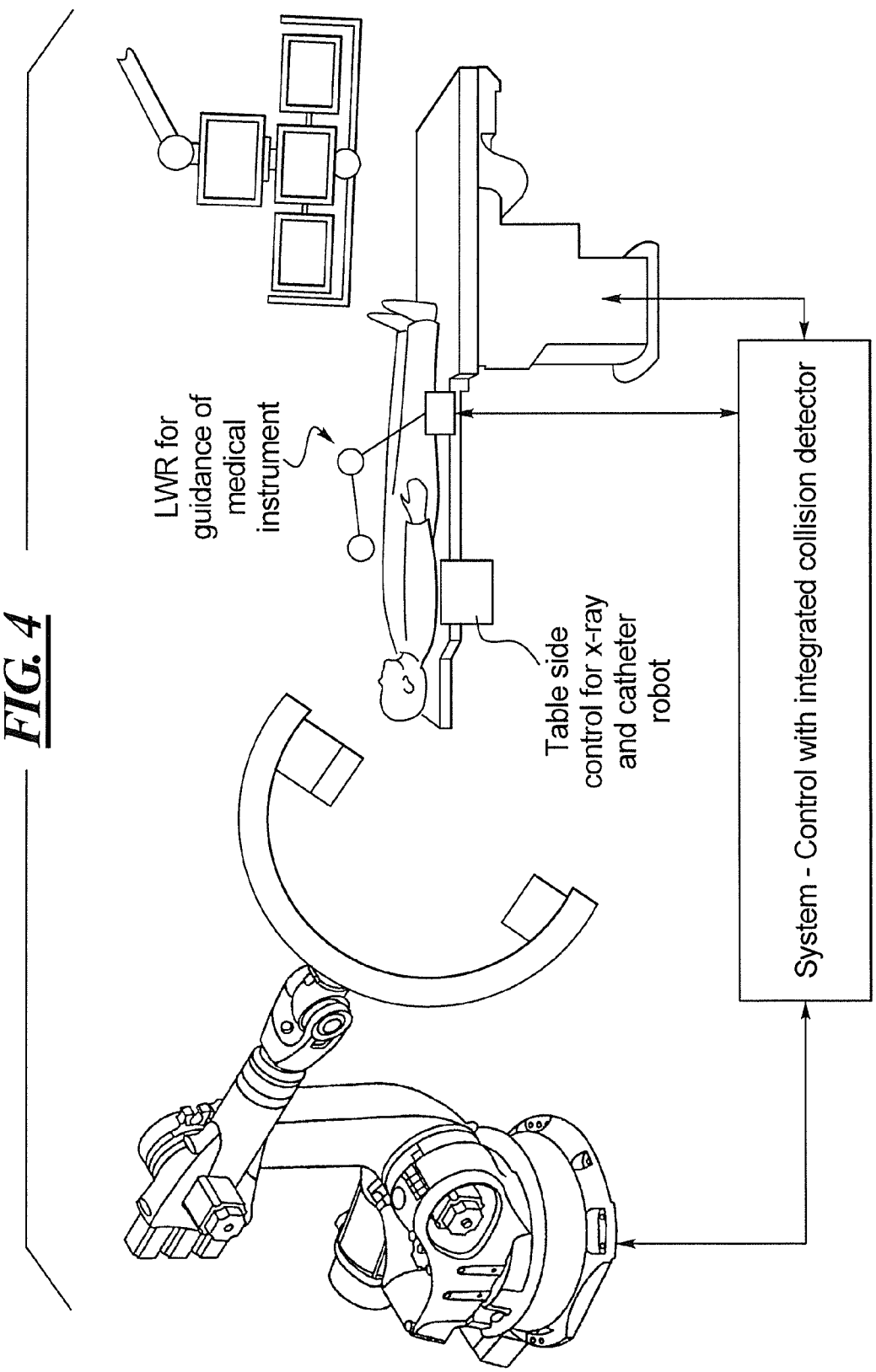
FIG. 4 schematically illustrates a robotically operated x-ray imaging system in accordance with the invention, for implementing the method in accordance with the invention.

An apparatus in accordance with the present invention for implementing the method according to the invention is shown in FIG. 4. This apparatus includes a robotically-operated x-ray imaging system shown at the left in FIG. 4, which includes an x-ray source and a radiation detector mounted on a C-arm, which can be arbitrarily moved with six degrees of freedom around an examination subject on a patient table, shown at the right side of FIG. 4. The robotically operated x-ray imaging system can be placed at a stationary position in order to obtain a "conventional" x-ray image, and also can be rotated through various projection angles to obtain a number of 2D projection images, that can then be combined in a known manner to form a reconstructed 3D image. In accordance with the invention, 3D images of the vessel or vessels in question, such as the gastric artery, are reconstructed as well as 3D images of the surrounding soft tissue, so as to allow clear visibility and differentiation of vessels and stomach tissue.

For generating a DSA image, as is well known, contrast agent is administered to the patient via a contrast agent injector, which is either automatically or manually controlled.

The position of the table is manually operated by a table-side control, which can also include wireless controls that communicate with the x-ray imaging system and with an LWR (light weight robot) for guidance of a medical instrument, such as a catheter in the case of the GACE procedure. Appropriate images are shown to be positioned by respective monitors shown at the right in FIG. 4.

Coordinated operation of all components, as is known, takes place by means of a system control, which can also have collision detection capability integrated therein to avoid injury to the patient and any other personnel in the environment of the moving C-arm.

Figure 5:
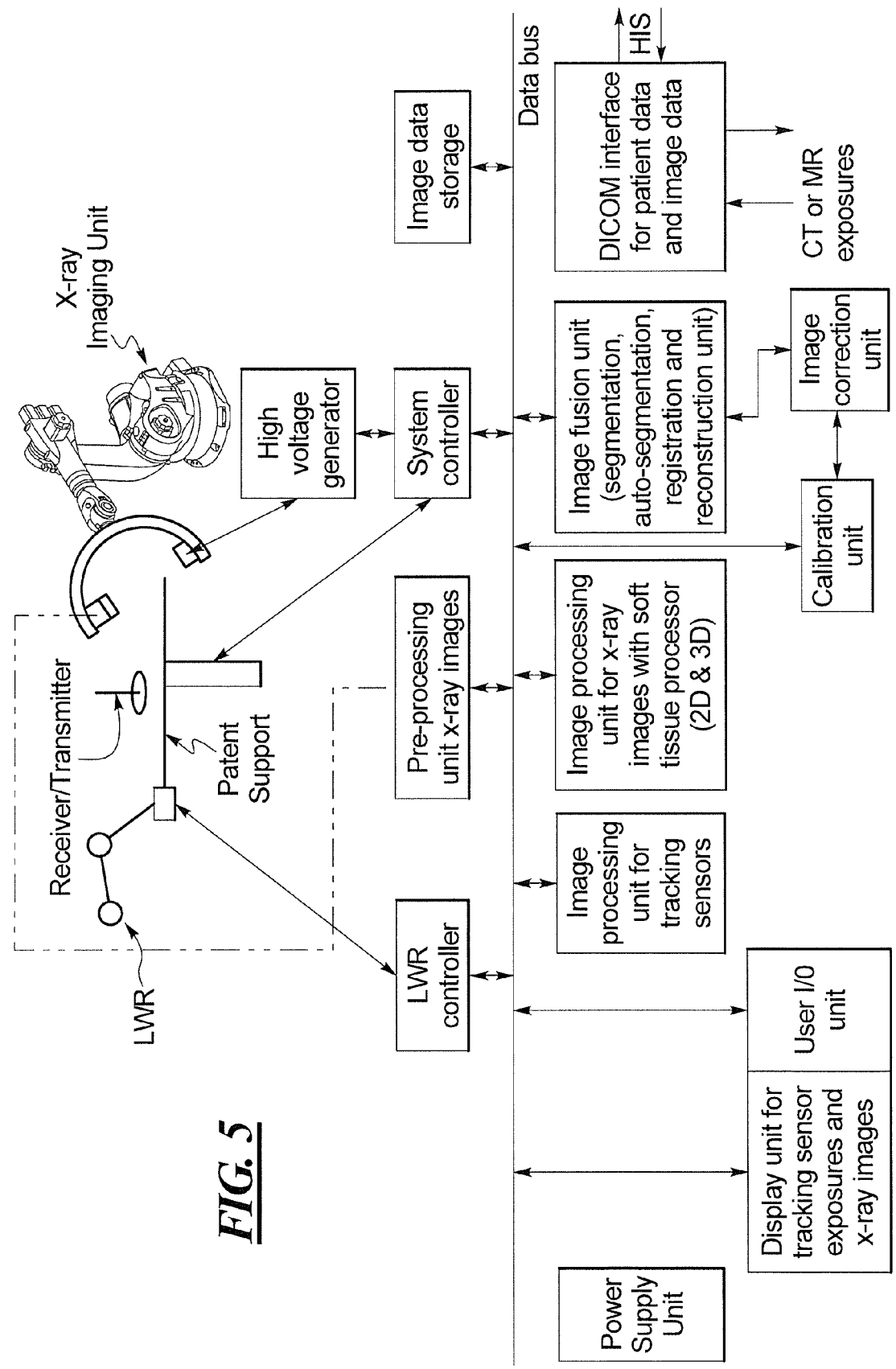
FIG. 5 is a block diagram showing the basic control and operating components of the imaging system of FIG. 4.

Further details of the system shown in FIG. 5 are shown in FIG. 4.

All components shown in FIG. 5 communicate with each other via a data bus.

The x-ray source is fed by a high voltage generator, which is operated by the system controller previously noted in FIG. 4, which also operates the patient support, in combination with the previously-noted manual control that is possible via the table-side control unit. The LWR is operated via an LWR controller.

X-ray images obtained with the radiation detector on the C-arm are supplied to a pre-processing unit for the x-ray images.

A receiver-transmitter is also schematically indicated in FIG. 5, which can be used to wirelessly, or via a cable, detect physiological functions of the patient, such as heart beat and respiration, via appropriate sensors attached to the patient. This information can be used for patient monitoring, and can also be used for gaiting the acquisition of the images in procedures where that is necessary. The receiver/transmitter communicates with an imaging processing unit for tracking sensors.

The acquired x-ray images are processed in an image processing unit, with a soft tissue processor. As noted above, 2D and/or 3D images can be generated in a known manner. Via the data bus, appropriate trigger information, or information for bringing images obtained in respective cardiac or respiratory cycles into registration from each other, can be provided by the image processing unit for tracking sensors.

An image fusion unit is also provided, that implements segmentation, auto-segmentation, registration and image reconstruction of fusion images. The necessary information for bringing such images into registration from each other is provided by a calibration unit, that is in communication with the image processing unit for tracking sensors via the data bus, and is also in communication with an image correction unit that communications with the image fusion unit.

The resulting images are supplied via the data bus to an image data storage for storage thereof.

A basic human interface unit is provided, that includes a user I/O unit, as well as the aforementioned display unit that includes the monitor shown in FIG. 4. A power supply unit is also indicated in FIG. 5, which provides power to all of the other units shown in FIG. 5 via appropriate cables. For clarity, all of those power connections are not specifically illustrated in FIG. 5.

A DICOM interface is also provided, via which patient data and previously-obtained image data can be received, either automatically or upon an appropriate request via the user I/O unit, from a data source, such as a hospital information system (HIS). The images obtained in accordance with the invented method can also be provided to the HIS via the DICOM interface, with appropriately-added DICOM headers. The DICOM interface also communicates with other imaging modalities that are not shown in FIG. 5, such as a CT exposure modality or an MR exposure modality. As with the power supply unit, the DICOM interface will communicate with many of the other components shown in FIG. 5, and, for clarity, those individual communication path or lines are omitted from FIG. 5.

The method according to the invention involves the following basic steps.

Before implementing the catheterization procedure, a first, current image data set of the fundus is obtained with an x-ray imaging system. This is preferably a 3D image dataset.

Subsequently, a second, current image dataset is obtained that shows the blood vessels that supply the fundus, with the gastric artery being highlighted. This second, current dataset may also be a 3D dataset.

The first and second current image datasets are fused to form a first fusion image dataset.

A second fusion image date set is then formed in which the current position of the catheter is made visible. Two embodiments are available in order to make the current position of the catheter visible in the second fusion image, which can be used individually or together. With the x-ray imaging system, a 2D image can be obtained in which the catheter is visible, such as by virtue of the catheter being provided with x-ray markings. Alternatively, position data of the catheter can be determined with a position determination device. Since the position determination device is in registration with the x-ray imaging device, the position data can be easily placed in relation to the first fusion image dataset.

The second fusion image dataset is then formed, by fusion of the first fusion image dataset with the aforementioned 2D dataset in which the catheter is visible and/or by using the position data in order to fuse the current position of the catheter with the first fusion image dataset. The resulting second fusion image dataset shows not only the fundus and the blood vessels supplying the fundus, but also the current position of the catheter.

Because the first current image dataset and the second current image dataset were acquired with the same x-ray imaging device, those images are already in registration without further measures being necessary.

3D image datasets of the stomach that were acquired in advance, and which show the fundus with good quality, but which are not current, may already exist. Such image datasets may have been acquired prior to the time of the treatment, such as for implementing a pre-treatment diagnosis. The information contained in these previously acquired image datasets can also be used for image assistance in the treatment by merging such a previously acquired 3D image dataset into the first fusion image dataset. For example, the first current image dataset (which also clearly shows the fundus) can be initially obtained or fused with the previously-acquired image dataset, so as to create an intermediate fusion image dataset. The intermediate fusion image dataset (which thus also includes the data of the first image dataset) is then fused with the second image dataset into the first fusion image dataset. The registration of the previously-acquired image dataset with the first current image dataset can take place using known registration techniques, such as by using anatomical landmarks such as points of the fundus or vessel outlets or branches.

The previously-acquired image dataset may have been generated, for example, by CT, MRI, PET, SPECT, ultrasound, PET-CT, SPECT-CT, PET-MRI, or SPECT-MRI.

The second fusion dataset is then displayed to a physician implementing the treatment, for use in guiding the catheter in the GACE procedure, and may even be automatically analyzed in a processor so as to generate guidance control information for robotic execution of the GACE procedure.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for gastric artery chemical embolization (GACE), comprising:
    before beginning a GACE catheterization procedure on a subject, operating an x-ray imaging system to acquire a first, current image data set of the fundus of the subject;
    also before beginning implementation of said GACE catheterization procedure, operating said x-ray imaging system to acquire a second current image data set that shows blood vessels that supply the fundus, and highlighting the gastric artery of the subject in said second current data set;
    providing said first current data set and said second current data set to a processor and, in said processor, fusing said first and second current image data sets to form a first fusion image data set;
    beginning said GACE catheterization procedure on said subject and, during said GACE catheterization procedure, acquiring a catheter position-indicating data set that includes a position of a catheter, used in said GACE catheterization procedure, in the subject;
    in said processor, fusing said first fusion image data set with said catheter position-indicating data set, to obtain a second fusion image in which the fundus and blood vessels that supply the fundus are visible and that shows a current position of the catheter in the subject relative to the fundus and the blood vessels that supply the fundus; and
    displaying said second fusion image during said GACE catheterization procedure at a location relative to the subject that allows a physician implementing the GACE catheterization procedure to view the second fusion image.

2. A method as claimed in claim 1 comprising operating said x-ray imaging system to generate said first current image data set as a 3D image data set.

3. A method as claimed in claim 1 comprising operating said x-ray imaging system to generate said second current image data set as a 3D image data set.

4. A method as claimed in claim 1 comprising operating said x-ray imaging system to generate said first current image data set as a first 3D image data set and to generate said second current image data set as a second 3D image data set.

5. A method as claimed in claim 1 comprising generating said catheter position-indicating data set as a 2D image acquired with said x-ray imaging system.

6. A method as claimed in claim 1 comprising generating said catheter-position-indicating data set using a navigation system that detects the position of the catheter in the subject and that generates position data designating said position of the catheter in the subject.

7. A method as claimed in claim 1 comprising, in said processor, automatically analyzing an image content of said second fusion image to generate control signals, and supplying said control signals to a lightweight robot and at least semi-automatically guiding the catheter in the subject with said lightweight robot during said GACE catheterization procedure.

8. A system for gastric artery chemical embolization (GACE), comprising:
    an x-ray imaging apparatus;
    a control unit configured, before beginning a GACE catheterization procedure on a subject, to operate the x-ray imaging apparatus to acquire a first, current image data set of the fundus of the subject;
    said control unit being configured to operate said x-ray imaging system also before beginning implementation of said GACE catheterization procedure, to acquire a second current image data set that shows blood vessels that supply the fundus, with the gastric artery of the subject highlighted in said second current data set;
    a processor provided with said first current data set and said second current data set, said processor being configured to fuse said first and second current image data sets to form a first fusion image data set;
    a catheter position-indicating data acquisition apparatus configured to acquire, during said GACE catheterization procedure, a catheter position-indicating data set that includes a position of a catheter, used in said GACE catheterization procedure, in the subject;
    said processor being configured to fuse said first fusion image data set with said catheter position-indicating data set, to obtain a second fusion image in which the fundus and blood vessels that supply the fundus are visible and that shows a current position of the catheter in the subject relative to the fundus and the blood vessels that supply the fundus;
    a display monitor in communication with said processor; and
    said processor being configured to display said second fusion image during said GACE catheterization procedure at said display monitor, said display monitor being situated at a location relative to the subject that allows a physician implementing the GACE catheterization procedure to view the second fusion image at the display monitor during the GACE catheterization procedure.

9. A system as claimed in claim 8 wherein said control unit is configured to operate said x-ray imaging apparatus to generate said first current image data set as a 3D image data set.

10. A system as claimed in claim 8 wherein said control unit is configured to operate said x-ray imaging apparatus to generate said second current image data set as a 3D image data set.

11. A system as claimed in claim 8 wherein said control unit is configured to operate said x-ray imaging apparatus to generate said first current image data set as a first 3D image data set and to generate said second current image data set as a second 3D image data set.

12. A system as claimed in claim 8 wherein said x-ray imaging apparatus forms said catheter position-indicating data acquisition apparatus and wherein said control unit is configured to generate said catheter position-indicating data set as a 2D image acquired with said x-ray imaging system.

13. A system as claimed in claim 8 wherein said catheter-position-indicating data acquisition apparatus is a navigation system configured to detect the position of the catheter in the subject and generate position data designating said position of the catheter in the subject.

14. A system as claimed in claim 8 wherein said x-ray imaging apparatus is a robotically-controlled C-arm x-ray apparatus.

15. A system as claimed in claim 8 comprising a lightweight robot configured to operate and guide said catheter at least semi-automatically dependent on robot control signals supplied to said lightweight robot from said processor, and wherein said processor is configured to automatically analyze an image content of said second fusion image data set and to generate said control signals from said image content.

\* \* \* \* \*